United States Patent
Bakki et al.

(10) Patent No.: US 12,329,559 B2
(45) Date of Patent: Jun. 17, 2025

(54) X-RAY IMAGING SYSTEM

(71) Applicant: KONINKLIJKE PHILIPS N.V., Eindhoven (NL)

(72) Inventors: Shailendra Kumar Bakki, Pune (IN); Johannes Köpnick, Neumünster (DE); Pavan Kumar Chivukula, Pune (IN); Eugene Hermann, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 432 days.

(21) Appl. No.: 17/639,597

(22) PCT Filed: Aug. 27, 2020

(86) PCT No.: PCT/EP2020/073918
§ 371 (c)(1),
(2) Date: Mar. 2, 2022

(87) PCT Pub. No.: WO2021/043655
PCT Pub. Date: Mar. 11, 2021

(65) Prior Publication Data
US 2022/0343676 A1  Oct. 27, 2022

(30) Foreign Application Priority Data
Sep. 3, 2019  (EP) .................................. 19195146

(51) Int. Cl.
*A61B 6/46*  (2024.01)
*A61B 5/1171*  (2016.01)
(Continued)

(52) U.S. Cl.
CPC ............ *A61B 6/468* (2013.01); *A61B 5/1176* (2013.01); *G06T 7/70* (2017.01); *G06V 10/242* (2022.01);
(Continued)

(58) Field of Classification Search
CPC .... A61B 6/468; A61B 5/1176; G06V 10/242; G06V 10/454; G06V 10/82; G06V 40/165;
(Continued)

(56) References Cited

U.S. PATENT DOCUMENTS 6,055,326 A   4/2000 Chang
10,172,578 B2  1/2019 Lee
(Continued)

FOREIGN PATENT DOCUMENTS

CN    107767416 A     3/2018
DE    102010007654 A1  8/2011
(Continued)

OTHER PUBLICATIONS

PCT International Search Report, International application No. PCT/EP2020/073918, Oct. 30, 2020.
(Continued)

*Primary Examiner* — Wassim Mahrouka
(74) *Attorney, Agent, or Firm* — Larry Liberchuk

(57) ABSTRACT

The present invention relates to an X-ray imaging system (10). The X-ray imaging system comprises an optical camera (20), an X-ray imaging device (30), a processing unit (40), and an output unit (50). The optical camera is configured to acquire an optical image of a body part (BP) of a patient or an optical image of the head of the patient. The X-ray imaging device is configured to acquire an X-ray image of the body part of the patient. The processing unit is configured to determine an orientation of the body part, the determination comprising utilization of the optical image of the body part or utilization of the optical image of the head of the patient. The processing unit is configured to annotate (Continued)

the X-ray image of the body part with the orientation. The output unit is configured to output the orientation annotated X-ray image.

15 Claims, 5 Drawing Sheets

(51) Int. Cl.
| | | |
|---|---|---|
| *G06T 7/70* | (2017.01) | |
| *G06V 10/24* | (2022.01) | |
| *G06V 10/44* | (2022.01) | |
| *G06V 10/82* | (2022.01) | |
| *G06V 40/16* | (2022.01) | |

(52) U.S. Cl.
CPC ............ *G06V 10/454* (2022.01); *G06V 10/82* (2022.01); *G06V 40/165* (2022.01); *G06V 40/166* (2022.01); *G06T 2207/10116* (2013.01); *G06T 2207/20084* (2013.01); *G06T 2207/30201* (2013.01); *G06V 2201/07* (2022.01)

(58) Field of Classification Search
CPC ............ G06V 40/166; G06V 2201/07; G06V 2201/03; G06T 2207/10116; G06T 2207/20084; G06T 2207/30201; G06T 7/73
See application file for complete search history.

(56) References Cited

U.S. PATENT DOCUMENTS

| | | |
|---|---|---|
| 10,830,712 B2 | 11/2020 | Butani |
| 11,605,179 B2 | 3/2023 | Anderson |
| 12,062,426 B2 | 8/2024 | Pagoulatos |
| 2007/0030957 A1 | 2/2007 | Pommi |
| 2013/0058545 A1 | 3/2013 | Pearson, Jr. |
| 2013/0163718 A1* | 6/2013 | Lindenberg .......... A61B 6/5235 378/39 |
| 2013/0173240 A1 | 7/2013 | Koell |
| 2015/0313566 A1 | 11/2015 | Diers |
| 2018/0158209 A1* | 6/2018 | Fine ..................... G16H 30/40 |
| 2018/0279883 A1* | 10/2018 | Navab ................. A61B 6/5247 |
| 2019/0167221 A1* | 6/2019 | Simon ..................... G06T 7/13 |
| 2020/0008676 A1* | 1/2020 | Dong .................. A61B 5/0035 |
| 2022/0198663 A1 | 6/2022 | Harada |
| 2023/0031744 A1* | 2/2023 | Joerger ................. G06F 18/25 |

FOREIGN PATENT DOCUMENTS

| | | |
|---|---|---|
| EP | 2130491 A1 | 9/2009 |
| EP | 3387997 A1 | 10/2018 |

OTHER PUBLICATIONS

Tugwell et al., "Radiographic Markers—A Reservoir for Bacteria?", Radiography, vol. 17, pp. 115-120, 2011.

* cited by examiner

PA or AP?

L or R?

X-RAY IMAGING SYSTEM

FIELD OF THE INVENTION

The present invention relates to an X-ray imaging system and a method of acquiring X-ray images.

BACKGROUND OF THE INVENTION

Radiographers need to take different views of different anatomical features of patients. The acquired X-ray images are annotated with respect to the view of the body part. Anterior-posterior view (AP view) is obtained with patient facing the X-ray tube of an X-ray imaging device with the cassette/detector behind the patient. The posterior-anterior view (PA view) is obtained with the patient facing the cassette/detector and with the X-ray tube behind the patient. Different views can be taken for better visualising the different anatomical features and sometimes can depend on the patient condition. R (right) and L (left) annotations of the X-ray image are used to determine the anatomical side of the body. This helps doctors and radiologists to interpret the X-ray images and provide diagnosis for planning the treatment on correct side of the patient.

For example when X-ray imaging a head of the patient Skull PA or Skull AP images can be acquired. And when imaging a hand PA or AP images can be acquired for the left or right hand. However, it can be difficult to tell from the X-ray image itself what the view was or indeed whether it was a right hand AP or a left hand PA view for example. In other words, the orientation of the body part cannot easily be determined from the acquired X-ray image itself. Therefore, normally a user needs to manually annotate the image. This is done with a metal symbol (L=left or R=right) such as a lead marker placed within the field of view prior to acquisition of the X-ray image or a manual software annotation of the acquired X-ray image using image processing software. However, this interrupts the user workflow, and radiographic lead markers have been suggested to be a potential fomite for harmful bacteria such as MRSA, and that they should be cleaned on a regular basis. This, however, is not always done: see for example Maddison & Tugwell. "Radiographic markers—A reservoir for bacteria?", Radiography; vol 17 pp 115-120, (2011). Also, errors can be made where a marker is placed incorrectly or whether post acquisition annotation is incorrect. There are also certain conditions that could lead to wrong-sided annotations of X-ray images, like: Situs inversus totalis; Dextro-cardia; and right sided Pneumoperitoneum. In these conditions, the heart and sometimes other organs appear to be on right side, as these are marks for detection of anatomical side in the X-ray images. Therefore, there is the potential that this could lead into wrong sided annotations, thus resulting in the wrong diagnosis, wrong sided intervention or sometimes unnecessary intervention leading to iatrogenic injuries and that could also be fatal in some cases. These also lead to increasing the cost and time of patient care.

There is a need to address these issues.

US 20130058545A1 describes a method for automatically determining an imaging orientation for a subject.

DE 102010007654A1 describes a digital medical imaging system with face recognition of a patient in order to determine the patient's orientation.

SUMMARY OF THE INVENTION

It would be advantageous to have an improved X-ray imaging system. The object of the present invention is solved with the subject matter of the independent claims, wherein further embodiments are incorporated in the dependent claims. It should be noted that the following described aspects and examples of the invention apply also to the X-ray imaging system and to the method of acquiring X-ray images medical image check apparatus.

In a first aspect, there is provided an X-ray imaging system, comprising:

an optical camera;
an X-ray imaging device;
a processing unit; and
an output unit.

The optical camera is configured to acquire an optical image of a body part (BP) of a patient or an optical image of the head of the patient. The X-ray imaging device is configured to acquire an X-ray image of the body part of the patient. The processing unit is configured to determine an orientation of the body part, the determination comprising utilization of the optical image of the body part or utilization of the optical image of the head of the patient. The determination further comprises utilization of the X-ray image of the body part. The processing unit is configured to annotate the X-ray image of the body part with the orientation. The output unit is configured to output the orientation annotated X-ray image.

In this manner, the orientation of the body part during acquisition of an X-ray image can be determined, when it can be very difficult to determine this only on the basis of the X-ray image itself.

In an example, the processing unit is configured to output via the output unit the determined orientation of the body part.

In this manner a check can be made that the patient has been correctly positioned for the X-ray scan. Thus, remedial action can be taken prior to the patient receiving any radiation dose.

In an example, the processing unit is configured to compare the determined orientation against an expected orientation of the body part. When the determined orientation does not match the expected orientation the processing unit is configured to output via the output unit an indication of the mismatch.

In other words, a scan protocol, for example, is referred to in order to determine what scan in terms of patient orientation is scheduled. Then the system can automatically check that the X-ray scan to be acquired is correct, and if not remedial action can be taken before the X-ray scan is undertaken.

It is to be noted that comparing the determined orientation against an expected orientation of the body part can also mean comparing an expected orientation of the body part against the determined orientation.

In an example, determination of the orientation of the body part comprises an extraction of anatomy specific features from the optical image.

In an example, the extraction comprises utilization of a known identification of the body part.

Thus, an efficient orientation determination can be made, where the most pertinent features for a specific body part enabling its orientation to be determined can be utilized.

In an example, determination of the orientation of the body part comprises a comparison of the anatomy specific features from the optical image with anatomy specific features from at least one database image for the identified body part.

In an example, determination of the orientation of the body part comprises utilization of a machine learning algorithm.

In an example, determination of the orientation of the body part comprises utilization of a trained neural network.

In an example, the neural network has been trained on the basis of optical images of the body part in a plurality of known orientations.

In an example, the neural network has been trained on the basis of optical images of a plurality of body parts each in a plurality of known orientations.

In an example, the neural network is a convolutional neural network.

In an example, the neural network is a fully convolutional neural network.

In an example, determination of the orientation of the body part comprises utilization of head and/or facial analysis software.

In an example, utilization of the facial analysis software comprises locating specific features in the optical image of the head of the patient, the specific features comprising at least one of: one or two eyes; nose; one or two nostrils; mouth; one or two lips; one or two ears; hairline.

Thus, locating certain features or indeed locating some and not others can enable it to be determined in which direction the person is looking. For example, locating both eyes in the centre of the head can be used to determine that the person is looking directly upwards, where such determination could be reinforced or alternatively made through locating the nose and/or mouth/lips etc. Locating a hairline towards the bottom of the head, adjacent to the torso, can be used to determine that the person is looking downwards, reinforced by the lack of determining eyes, nose and mouth, but indicating that the person is looking directly downwards if both ears were located. Other variations of features located, and their spatial position with respect to the overall head and/or spatial orientation relative to each other can be used to determine whether the person is looking right or left, and indeed whether they are looking down and to the right, or up and to the right, for example.

In an example, the orientation of the body part is determined with respect to an imaging axis of the X-ray imaging device.

In an example, an imaging axis of the optical camera is known with respect to the imaging axis of the X-ray imaging device.

In other words, the position and line of sight of the optical camera is known with respect to the position and line of sight of the X-ray imaging device, thereby enabling a simple transformation of an orientation of the body part with respect to the optical camera to be transformed to an orientation of the body part with respect to the X-ray imaging device.

In a second aspect, there is provided a method of acquiring X-ray images, comprising:
  a) acquiring by an optical camera an optical image of a body part of a patient or an optical image of the head of the patient;
  b) determining by a processing unit an orientation of the body part, the determining comprising utilizing the optical image of the body part or utilizing the optical image of the head of the patient; wherein the determination further comprises utilization of the X-ray image of the body part;
  d) acquiring by an X-ray imaging device an X-ray image of the body part of the patient;
  e) annotating by the processing unit the X-ray image of the body part with the orientation; and
  f) outputting by an output unit the orientation annotated X-ray image.

According to another aspect, there is provided a computer program element controlling one or more of the systems as previously described which, if the computer program element is executed by a processing unit, is adapted to perform one or more of the methods as previously described.

According to another aspect, there is provided a computer readable medium having stored computer element as previously described.

The computer program element can for example be a software program but can also be a FPGA, a PLD or any other appropriate digital means.

Advantageously, the benefits provided by any of the above aspects equally apply to all of the other aspects and vice versa.

The above aspects and examples will become apparent from and be elucidated with reference to the embodiments described hereinafter.

BRIEF DESCRIPTION OF THE DRAWINGS

Exemplary embodiments will be described in the following with reference to the following drawings.

DETAILED DESCRIPTION OF THE EMBODIMENTS

Figure 1:
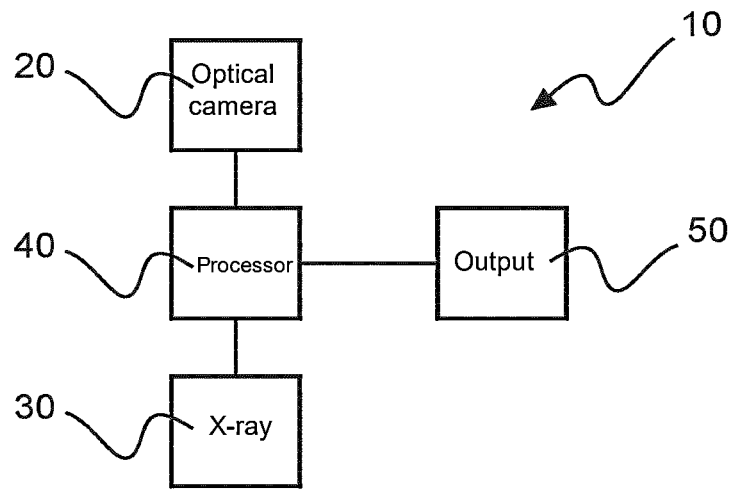
FIG. 1 shows a schematic set up of an example of an X-ray imaging system.

FIG. 1 shows an example of an X-ray imaging system 10. The X-ray imaging system comprises an optical camera 20, an X-ray imaging device 30, a processing unit 40, and an output unit 50. The optical camera is configured to acquire an optical image of a body part (BP) of a patient or an optical image of the head of the patient. The X-ray imaging device is configured to acquire an X-ray image of the body part of the patient. The processing unit is configured to determine an orientation of the body part. The determination comprises utilization of the optical image of the body part or utilization of the optical image of the head of the patient. The processing unit is configured also to annotate the X-ray image of the body part with the orientation. The output unit is configured to output the orientation annotated X-ray image.

In an example, the optical image of the head of the patient comprises an optical image of the face of the patient.

According to the invention, the determination of the orientation of the body part comprises utilization of the X-ray image data of the body part.

Thus, even though the X-ray image itself is not sufficient to determine the orientation of the body part, the X-ray image data augments the optical image data to determine the orientation of the body part. Thus, for example the X-ray image data can be utilized to aid processing of the optical imagery by selecting which part of the optical image of the body part should be processed to determine its orientation. In this situation, the use of the X-ray image occurs after the optical image acquisition and it has been found that this is not essential, and body part orientation determination can proceed on the basis of the optical image data alone. However, in certain situations the X-ray data can aid in that orientation determination.

The X-ray image data can be DICOM metadata from the X-ray image (which was either produced automatically or manually by the user) or the X-ray image itself, where for example output from an algorithm which analyses the X-ray image is used as an input to the optical image processing.

In an example, annotation of the X-ray image comprises storing the determined orientation in metadata of the X-ray image, for example in the DICOM image header.

According to the invention, the processing unit is configured to determine an identification of the body part. The determination comprises utilization of the X-ray image of the body part and utilization of the optical image of the body part.

Thus, the body part being examined can be determined/verified and this information can aid in the processing of optical imagery, with the X-ray imagery, in order to determine the orientation of the body part. In this manner, a fully automated, robust body part orientation system is provided.

In an example, the output unit is configured to output the identified body part, such as for example: skull, leg, arm, or other body part.

According to an example, the processing unit is configured to output via the output unit the determined orientation of the body part.

According to an example, the processing unit is configured to compare the determined orientation against an expected orientation of the body part. When the determined orientation does not match the expected orientation the processing unit is configured to output via the output unit an indication of the mismatch.

According to an example, determination of the orientation of the body part comprises an extraction of anatomy specific features from the optical image.

According to an example, the extraction comprises utilization of a known identification of the body part.

In an example, the known identification of the body part is that the body part is a hand of the patient.

In an example, the known identification of the body part is that the body part is a head of the patient.

In an example, the known identification of the body part is that the body part is a leg of the patient.

In an example, the known identification of the body part is that the body part is the chest of the patient.

In an example, the body part can be spine, pelvis, hip, femur, foot, shoulder or shoulders, arm or arms, or other body parts.

According to an example, determination of the orientation of the body part comprises a comparison of the anatomy specific features from the optical image with anatomy specific features from at least one database image for the identified body part.

In an example, the database image for the identified body part is provided in an anatomical orientation.

In an example, database images for the identified body parts are provided in a number of different anatomical orientations.

In an example, anatomical orientations include: left hand, right hand, anterior-posterior chest, posterior-anterior chest and foot dorso-plantar. Other orientations are possible.

According to an example, determination of the orientation of the body part comprises utilization of a trained neural network.

According to an example, the neural network has been trained on the basis of optical images of the body part in a plurality of known orientations.

According to an example, the neural network has been trained on the basis of optical images of a plurality of body parts each in a plurality of known orientations.

According to an example, the neural network is a convolutional neural network.

According to an example, determination of the orientation of the body part comprises utilization of facial analysis software.

According to an example, utilization of the facial analysis software comprises locating specific features in the optical image of the head of the patient. The specific features comprises at least one of: one or two eyes; a nose; one or two nostrils; a mouth; one or two lips; one or two ears; hairline.

According to an example, the orientation of the body part is determined with respect to an imaging axis 32 of the X-ray imaging device.

According to an example, an imaging axis 22 of the optical camera is known with respect to the imaging axis of the X-ray imaging device.

Figure 2:
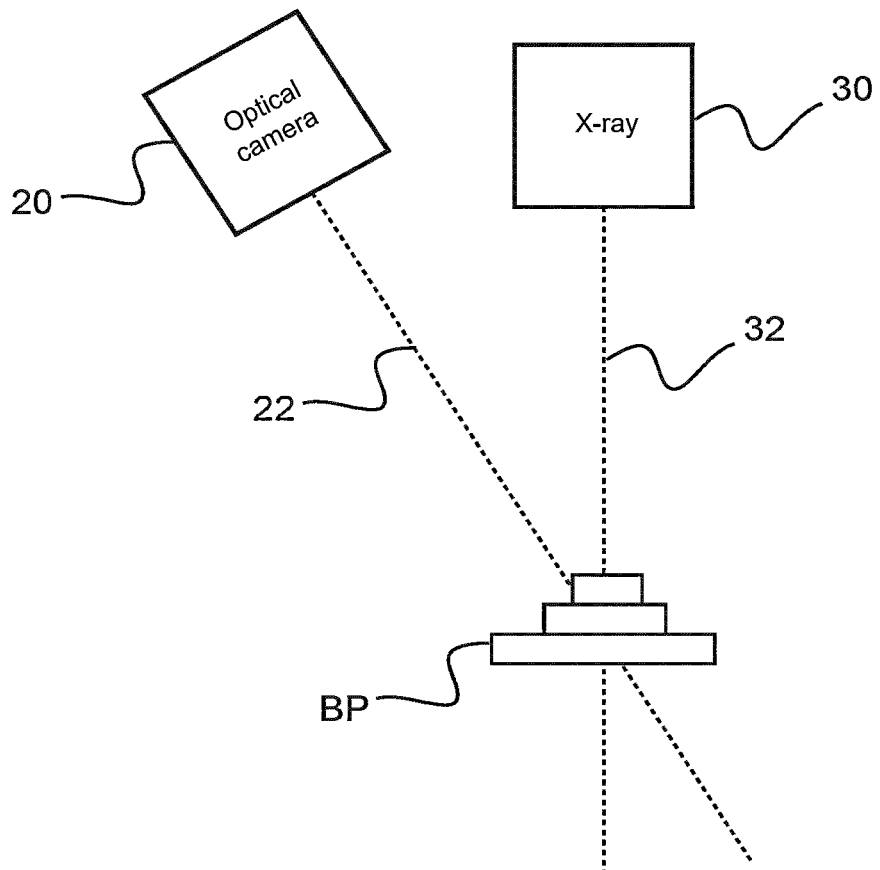
FIG. 2 shows a schematic set up of line of sight axes of an optical camera and an X-ray imaging device of an example of an X-ray imaging system.

FIG. 2 shows more detail of the optical camera 20 and an X-ray imaging device 30 acquiring imagery of the body part (BP). As imaging axis 32 of the X-ray imaging device is shown extending through the body part, and an imaging axis 22 of the optical camera is shown extending through the body part. From an X-ray image acquired of the body part it is very difficult to determine the orientation of the object. Thus, referring to FIG. 2 it is very difficult to determine which layer is on top of which layer, in that the order of layers could be reversed and indeed the smallest layer could be in the middle or the largest layer could be in the middle. However, by acquiring an optical image the orientation of the object can be determined and this can be aided when the axial orientation of the optical camera is known with respect to that of the X-ray imaging device.

Figure 3:
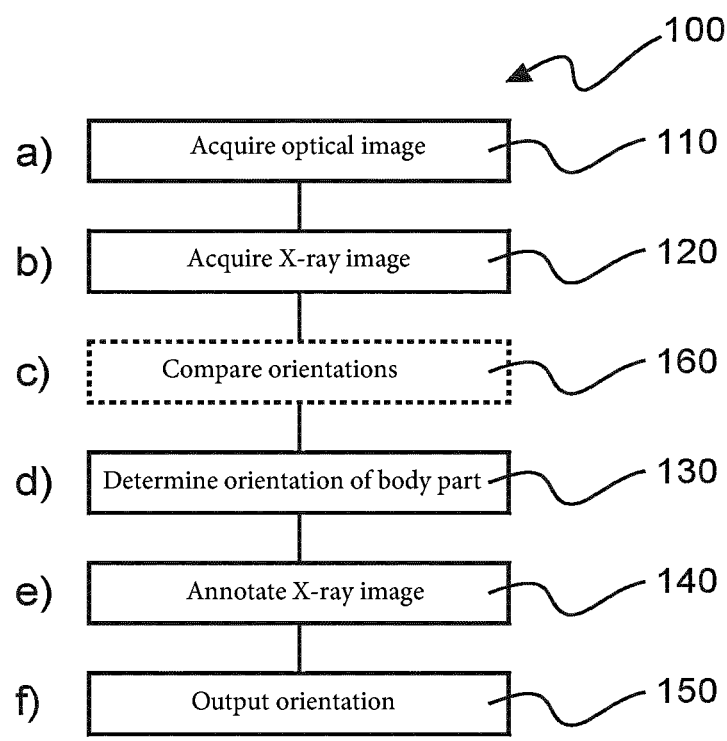
FIG. 3 shows a method of acquiring X-ray images.

FIG. 3 shows a method 100 of acquiring X-ray images in its basic steps where essential steps are shown in solid lines and optional steps are shown in dashed lines. The method comprises:

in an acquiring step 110, also referred to as step a), acquiring by an optical camera an optical image of a body part of a patient or an optical image of the head of the patient;

in a determining step 120, also referred to as step b), determining by a processing unit an orientation of the body part, the determining comprising utilizing the optical image of the body part or utilizing the optical image of the head of the patient; in an acquiring step 130, also referred to as step d), acquiring by an X-ray imaging device an X-ray image of the body part of the patient;

in an annotating step 140, also referred to as step e), annotating by the processing unit the X-ray image of the body part with the orientation; and in an outputting step 150, also referred to as step f), outputting by an output unit the orientation annotated X-ray image.

In an example, step f) comprises outputting by the output unit the determined orientation of the body part.

In an example, the method comprises step c), comparing 160 by the processing unit configured the determined orientation against an expected orientation of the body part and wherein when the determined orientation does not match the expected orientation the processing unit is configured to output via the output unit an indication of the mismatch.

In an example, step b) comprises extracting anatomy specific features from the optical image.

In an example, the extracting comprises utilizing a known identification of the body part.

In an example, step b) comprises comparing the anatomy specific features from the optical image with anatomy specific features from at least one database image for the identified body part.

In an example, step b) comprises utilizing a trained neural network.

In an example of the method, the neural network has been trained on the basis of optical images of the body part in a plurality of known orientations.

In an example of the method, the neural network has been trained on the basis of optical images of a plurality of body parts each in a plurality of known orientations.

In an example of the method, the neural network is a convolutional neural network.

In an example, step b) comprises utilizing facial analysis software.

In an example, utilizing the facial analysis software comprises locating specific features in the optical image of the head of the patient, the specific features comprising at least one of: one or two eyes; nose; one or two nostrils; mouth; one or two lips; one or two ears; hairline.

In an example, in step b) the orientation of the body part is determined with respect to an imaging axis of the X-ray imaging device.

In an example, an imaging axis of the optical camera is known with respect to the imaging axis of the X-ray imaging device.

The X-ray imaging system and the method of acquiring X-ray images are now described with respect to specific embodiments, where reference is made to FIGS. 4-10.

Figure 4:
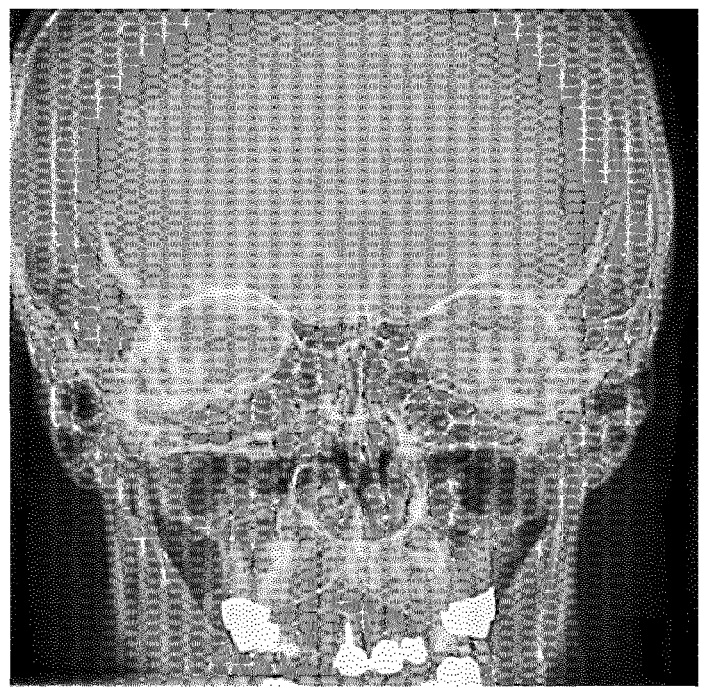
FIG. 4 shows an exemplar X-ray image of a head.
Figure 5:
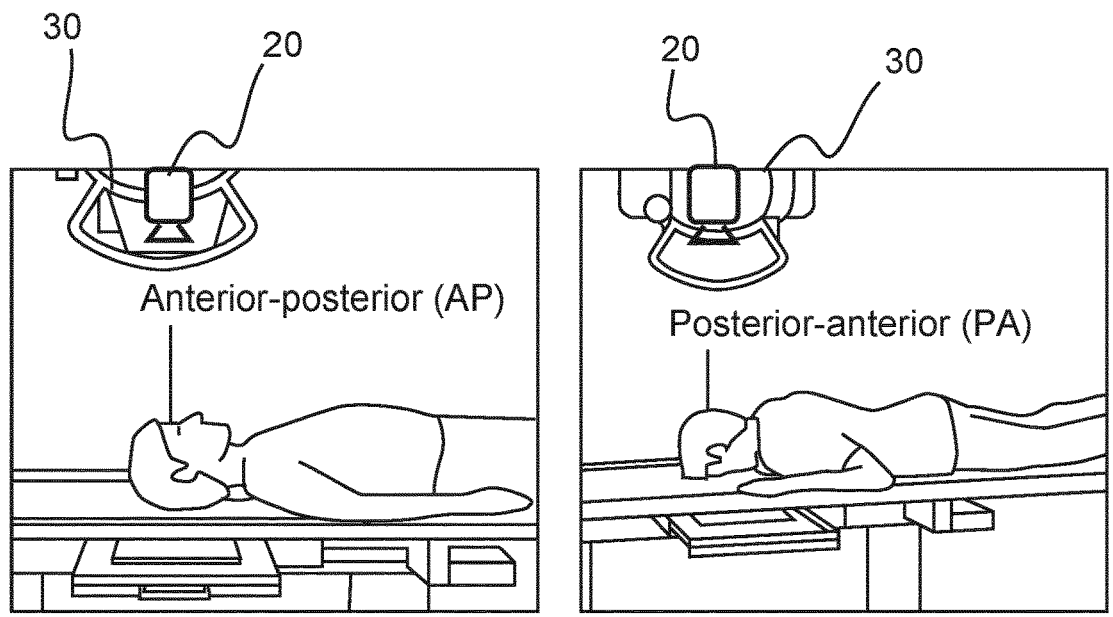
FIG. 5 shows a schematic set up of an example of an X-ray imaging system.
Figure 6:
FIG. 6 shows an exemplar X-ray image of a hand.
Figure 7:
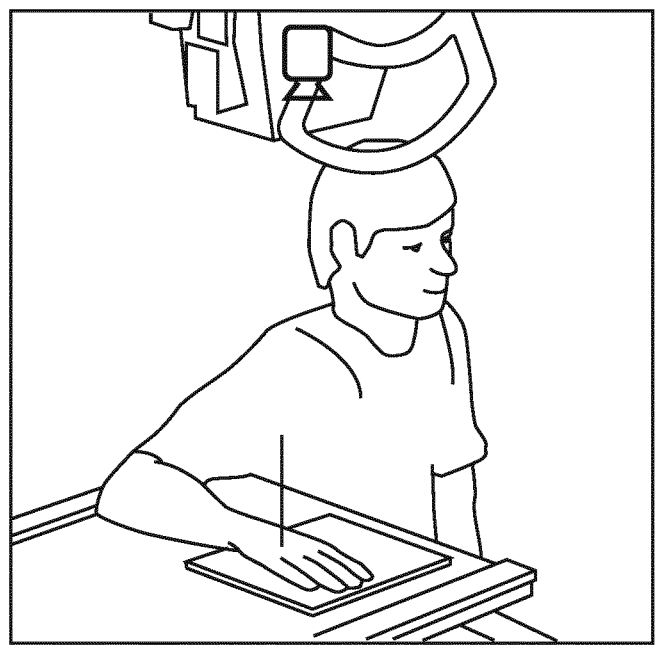
FIG. 7 shows a schematic set up of an example of an X-ray imaging system.

FIG. 4 shows an X-ray image of the head of a patient. From this image it is difficult to determine the orientation—is it PA or AP? However, the X-ray imaging system and the method of acquiring X-ray images addresses this as shown in FIG. 5 where an optical camera is acquiring an image of the patient. This can be taken before the X-ray image is acquired in order that it can be determined if the patient is correctly placed for the examination, or it can be taken simultaneously with the X-ray image acquisition. The digital image or photo, or indeed images/photos from the camera provides additional information (surface, colour, contours, and shape) which can be used to determine (via Image Vision Software) whether the patient is looking towards (Skull AP) or away from the X-ray source/tube (Skull PA). FIG. 6 shows the equivalent situation for imaging a hand, where from the X-ray image it is difficult to determine if it is the right hand or left hand that has been imaged. Again, the X-ray imaging system and the method of acquiring X-ray images addresses this as shown in FIG. 7 where an optical image of the hand is acquired, and analysis then determines if the palm of the hand is facing towards or away from the X-ray source/tube. In this way there is no need for the user to manually annotate leading to improved workflow, and there is no risk of false or missing annotations.

Thus in effect the system and method uses a camera image taken from the anatomy synchronically (or slightly timed before) with the X-ray image. It analyses this image and determines the orientation of the anatomy (e.g. left or right hand, PA or AP Chest) and the result is stored in the X-ray image meta data. This can be used to give a feedback on the anatomy orientation through the user interface before the X-ray is taken to prevent that a wrong examination is performed (e.g. right hand instead of left hand, chest AP instead of chest PA). This can be done by comparing the results from the invention with a database entry from the patient; Picture Archiving and Communication System (PACS), or RISK.

The analysis of the video frames/images can be implemented in different ways. A model-based or an AI approach can be used:

Model-based approach: Prior knowledge about the anatomy can be utilized. That information is given by the type of selected examination. Depending on the anatomy, anatomy-specific characteristics are extracted from the image, first. Then, the orientation of the anatomy can be obtained by using the different models.

Artificial Intelligence approach: Different anatomies with the appropriate anatomical orientation are trained using a Convolutional Neural Network. A new image, more precisely the anatomical orientation in the new image, is then classified using the trained model.

As discussed above, a digital camera can be used to obtain digital images. These the digital images can then be processed using digital image processing and image analysis algorithms such as image segmentation, feature extraction, image pattern classification and many more to determine the orientation of the body part.

However, it was realised that recent advances in head and face image analysis, techniques and technologies could be used to extract certain facial features like location of eyes (right and left), nose including nostrils and lips, whether the person is facing away from the camera, and this could be made use of. Thus, head and face image analysis technologies can be used for the detection of anatomical side location and type of view for automatic and correct annotation of X-ray images.

Figure 8:
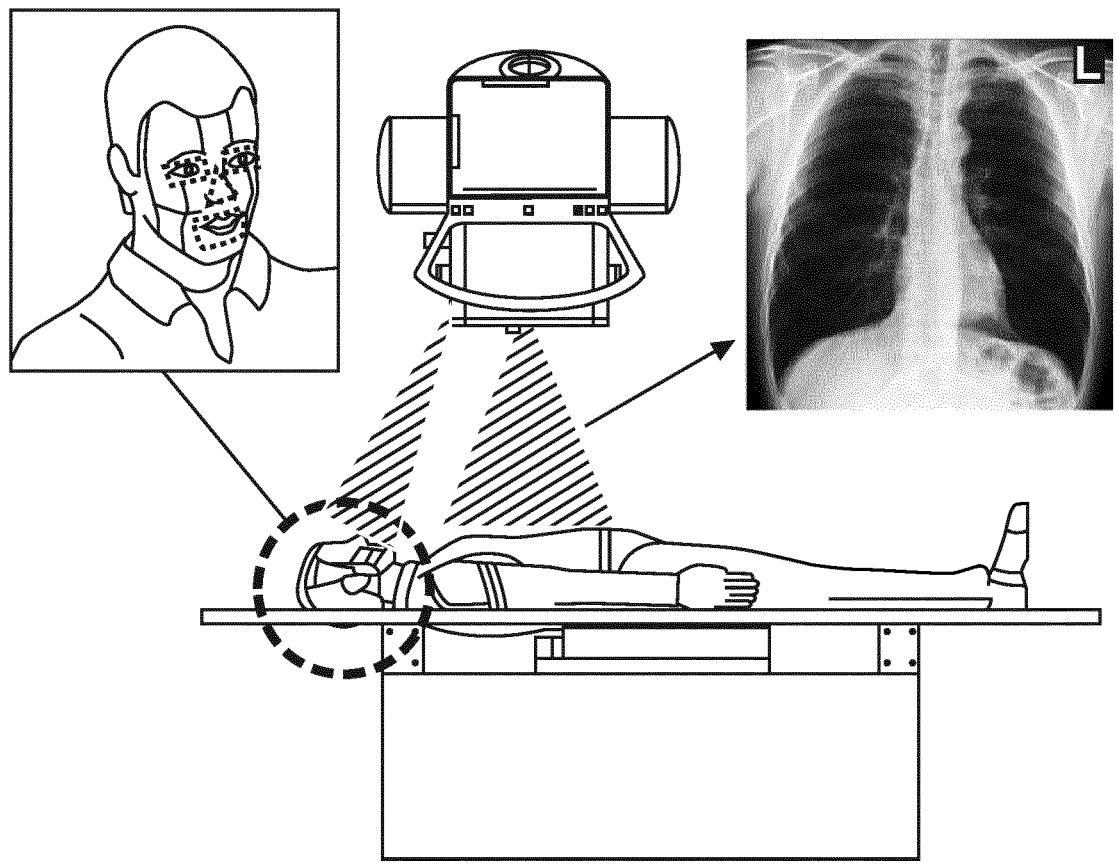
FIG. 8 shows a schematic set up of an example of an X-ray imaging system.

FIG. 8 shows an example of an X-ray imaging system that makes use of this functionality. A Camera is mounted in X-ray room or on the X-ray tube head or at another location to capture imagery to locate facial features. The different facial features considered for extraction are the eyes (right and left), nose including the nostrils and lips. In total the information collected are:

Eyes (right and Left)—2

Nose including nostrils—3

Lips (upper and lower)—2

The selection of multiple features can help, when the analysis algorithm operates, to provide a higher confidence level that the head and/or face has been detected in order to determine the patient position. The face image can de-identified to protect the patient privacy, as the information of facial features location is enough to determine the patient view and side location.

Thus, the digital camera is oriented and placed in a known way with respect to the X-ray tube/source. The digital images captured through the camera are processed and analysed for facial feature or facial landmarks extraction. This extracted information is used to identify patient orientation with respect to the X-ray tube/source. Thus, the anatomical side could be identified to be used as automated right and left annotation markings over the X-ray image. As shown in FIG. 8 the imagery of the head and/or face can be used to determine if the patient is lying on their back, on their front, on their left side or on their right side. The X-ray image can be of the head, and for the patient lying on their front or back the imagery can be used to determine their orientation as discussed above, when that would be difficult from the X-ray imagery itself. However, the new technique finds utility when the X-ray image is to be taken of a different body part to the head. Thus, for example as shown on FIG. 8 optical image analysis of the head and/or face can determine if the patient is lying on their front or back and this can be used to automatically annotate an acquired chest X-ray with the correct orientation.

Figure 9:
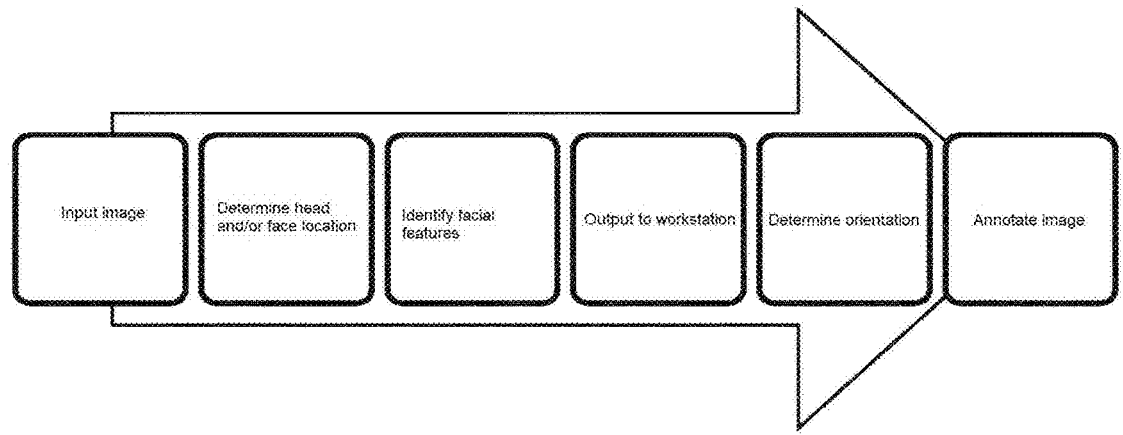
FIG. 9 shows a detailed workflow of a method of acquiring X-ray images.
Figure 10:
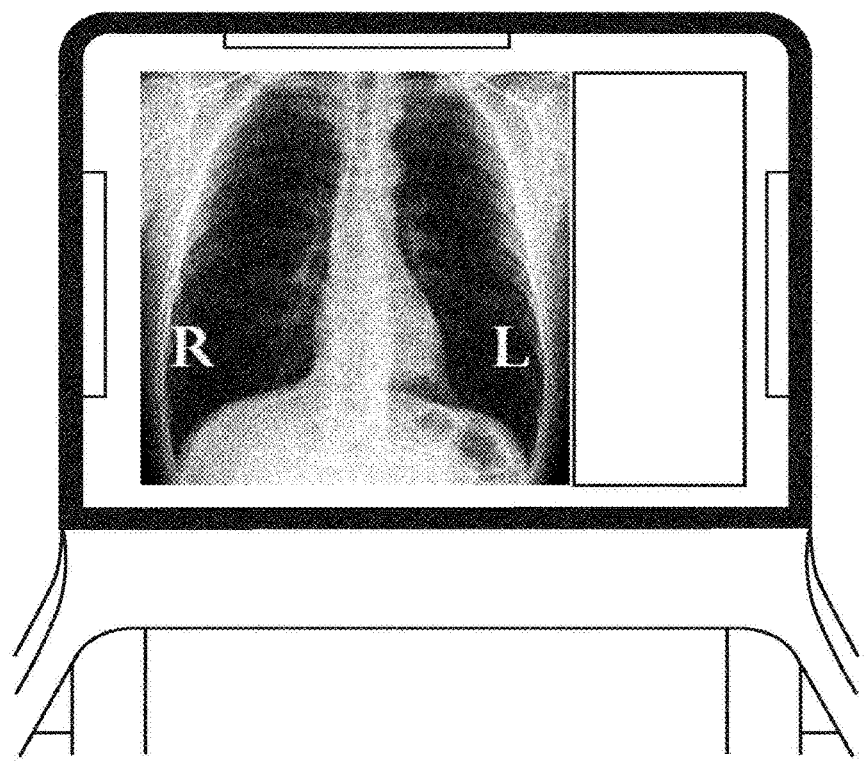
FIG. 10 shows an exemplar output from the system and method of acquiring X-ray images.

FIG. 9 shows a detailed workflow relating to a detailed method of acquiring X-ray images. At step "A" an image is input, at step "B" head and/or face location is determined, and at step "C" facial features identified (eyes, nostrils and mouth). At step "D" the output details centre workstation, where at step "E" processing is carried out to determine the orientation, and at step "F" the X-ray images annotated for example with AP/PA for an orientation of the head with respect to the X-ray tube location.

The camera captures the image and facial features with extraction providing the information regarding the AP and PA view. The orientation of facial features w.r.t X-ray tube provides the patient right side and left side information.

Thus the following provides a possible annotation flow protocol.
1. acquire optical image
2. analyse optical image
3. have facial features been identified
    a. No
        i AP View
        ii orientation with respect to the X-ray tube is determined
            1. Left, or
            2. Right
    b. Yes
        i PA View
        ii orientation with respect to the X-ray tube is determined
            1. Left, or
            2. Right FIG. 10 then shows the final orientation annotated image, where the image can be annotated as PA and/or annotated with R and L as shown.

In another exemplary embodiment, a computer program or computer program element is provided that is characterized by being configured to execute the method steps of the method according to one of the preceding embodiments, on an appropriate system.

The computer program element might therefore be stored on a computer unit, which might also be part of an embodiment. This computing unit may be configured to perform or induce performing of the steps of the method described above. Moreover, it may be configured to operate the components of the above described apparatus and/or system. The computing unit can be configured to operate automatically and/or to execute the orders of a user. A computer program may be loaded into a working memory of a data processor. The data processor may thus be equipped to carry out the method according to one of the preceding embodiments.

This exemplary embodiment of the invention covers both, a computer program that right from the beginning uses the invention and a computer program that by means of an update turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, USB stick or the like, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An X-ray imaging system, comprising:
    an optical camera configured to acquire an optical image of a body part of a patient;
    an X-ray imaging device configured to acquire an X-ray image of the body part of the patient;
    a processor configured to determine an orientation of the body part based on the optical image and the X-ray image, wherein the X-ray image is used to aid in processing the optical image by selecting which part of the optical image of the body part is to be processed in order to determine the orientation, and wherein the processor is configured to annotate the X-ray image with the orientation; and a display configured to output the annotated X-ray image only.

2. The system according to claim 1, wherein the processor is configured to output via the display the determined orientation of the body part.

3. The system according to claim 1, wherein the processor is configured to compare the determined orientation and an expected orientation of the body part, and wherein when the determined orientation does not match the expected orientation the processor is configured to output via the display an indication of a mismatch.

4. The system according to claim 1, wherein determination of the orientation of the body part comprises an extraction of anatomy specific features from the optical image.

5. The system according to claim 4, wherein the extraction comprises utilization of a known identification of the body part.

6. The system according to claim 5, wherein determination of the orientation of the body part comprises a comparison of the anatomy specific features from the optical image with anatomy specific features from at least one database image for the identified body part.

7. The system according to claim 1, wherein determination of the orientation of the body part comprises utilization of a trained neural network.

8. The system according to claim 7, wherein the neural network is trained based on optical images of the body part in a plurality of known orientations.

9. The system according to claim 7, wherein the neural network is trained based on optical images of a plurality of body parts each in a plurality of known orientations.

10. The system according to claim 7, wherein the neural network is a convolutional neural network.

11. The system according to claim 1, wherein determination of the orientation of the body part comprises utilization of facial analysis software.

12. The system according to claim 11, wherein utilization of the facial analysis software comprises locating specific features in the optical image of the patient, the specific features comprising at least one of: one or two eyes, nose, one or two nostrils, mouth, and one or two lips.

13. The system according to claim 1, wherein the orientation of the body part is determined with respect to an imaging axis of the X-ray imaging device.

14. The system according to claim 13, wherein the imaging axis of the optical camera is known with respect to an imaging axis of the X-ray imaging device.

15. A computer-implemented method of acquiring X-ray images, comprising:

acquiring by an optical camera an optical image of a body part of a patient;

acquiring by an X-ray imaging device an X-ray image of the body part;

determining by a processor an orientation of the body part based on the optical image and the X-ray image, wherein the X-ray image is used to aid in processing the optical image by selecting which part of the optical image is to be processed in order to determine the orientation;

annotating by the processor the X-ray image with the orientation; and outputting the annotated X-ray image only.

* * * * *